United States Patent [19]

Whitlock

[11] Patent Number: 4,874,507

[45] Date of Patent: Oct. 17, 1989

[54] SEPARATING CONSTITUENTS OF A MIXTURE OF PARTICLES

[76] Inventor: David R. Whitlock, 138 Vassal La., Cambridge, Mass. 02138

[21] Appl. No.: 174,601

[22] Filed: Mar. 29, 1988

Related U.S. Application Data

[63] Continuation-in-part of Ser. No. 872,082, Jun. 6, 1986.

[51] Int. Cl.$^4$ .................... B03C 9/00; B01D 17/00
[52] U.S. Cl. .................... 209/11; 204/157.3; 204/158.2; 204/180.1; 204/182.3; 204/182.6; 204/183.1; 204/183.2; 204/299 R; 204/302; 204/307; 204/308; 209/127.1; 209/212; 209/214
[58] Field of Search ............... 209/3, 11, 127.1–127.4, 209/128–131, 212, 214, 225, 231, 155, 208, 210; 210/748; 241/23, 24, 79.1; 204/157.3, 158.2, 180.1, 181.8, 181.9, 182.3, 182.4, 182.6, 183.1–183.3, 299 R, 302, 207, 308

[56] References Cited

U.S. PATENT DOCUMENTS

| | | | |
|---|---|---|---|
| 1,100,896 | 9/1914 | Comstock | 209/129 |
| 1,222,305 | 4/1917 | Kraus | 209/127.4 X |
| 1,355,477 | 10/1920 | Howell | 209/127.3 X |
| 2,689,648 | 9/1954 | Maestas | 209/131 |
| 2,847,124 | 8/1958 | Brastad | 209/127.1 |
| 2,889,042 | 6/1959 | Le Baron | 209/127.1 |
| 3,022,889 | 2/1962 | Le Baron et al. | 209/127.1 X |
| 3,140,714 | 7/1964 | Murphy, Jr. et al. | 209/2 UX |
| 3,247,960 | 4/1966 | Brastad | 209/11 |
| 3,449,938 | 6/1969 | Giddings . | |
| 3,493,109 | 2/1970 | Carta et al. | 209/127.1 X |
| 3,635,340 | 1/1972 | Dunn | 209/130 |
| 3,664,939 | 5/1972 | Luner et al. | 204/299 X |
| 4,122,002 | 10/1978 | Hauskins, Jr. | 209/127.1 X |
| 4,137,156 | 1/1979 | Morey et al. | 209/212 |
| 4,172,028 | 10/1979 | Dunn | 209/127.1 X |
| 4,302,245 | 11/1981 | Winters | 209/214 X |
| 4,358,358 | 11/1982 | Rhodes | 204/180.1 X |
| 4,440,638 | 4/1984 | Judy et al. | 204/302 X |
| 4,476,004 | 10/1984 | Pohl | 204/302 X |
| 4,533,447 | 8/1985 | Meldon | 204/302 X |

FOREIGN PATENT DOCUMENTS

| | | | |
|---|---|---|---|
| 0705007 | 4/1941 | Fed. Rep. of Germany | 209/127.3 |
| 0495088 | 3/1976 | U.S.S.R. | 209/131 |
| 0498042 | 3/1976 | U.S.S.R. | 209/131 |
| 1196033 | 12/1985 | U.S.S.R. | 209/127.1 |

OTHER PUBLICATIONS

SME Mineral Processing Handbook—Norman L. Weiss, Pub. by Society of Mining Engineers of the American Institute of Mining, Metallurgical, and Petroleum Engineers, Inc., 1985, pp. 6–34.

Primary Examiner—Dennis H. Pedder
Assistant Examiner—Edward M. Wacyra
Attorney, Agent, or Firm—Wolf, Greenfield & Sacks

[57] ABSTRACT

The specification describes specie-separating and concentration-enhancing methods and apparatus which operate on a substantially continual basis. The constituents of a mixture are separated according to their respective influencability by motion in the direction of a separation influence and the species of like net influencability are transported in substantially continuous streams, each of opposite net influencability running near each other, in a direction or directions transverse to the separation influence, the streams being in communication parallel to the separation influence so as to transfer at least one of the separable species from one stream to another stream by virtue of continued separation of influenceable species as the respective streams progress transversely to the separation influence. The two streams can run in the same direction (co-current) or in respectively opposite directions (countercurrent).

42 Claims, 9 Drawing Sheets

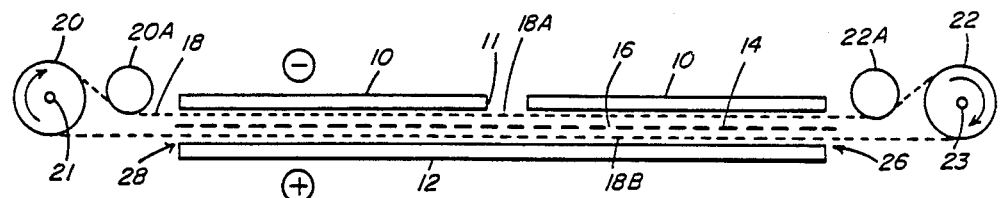
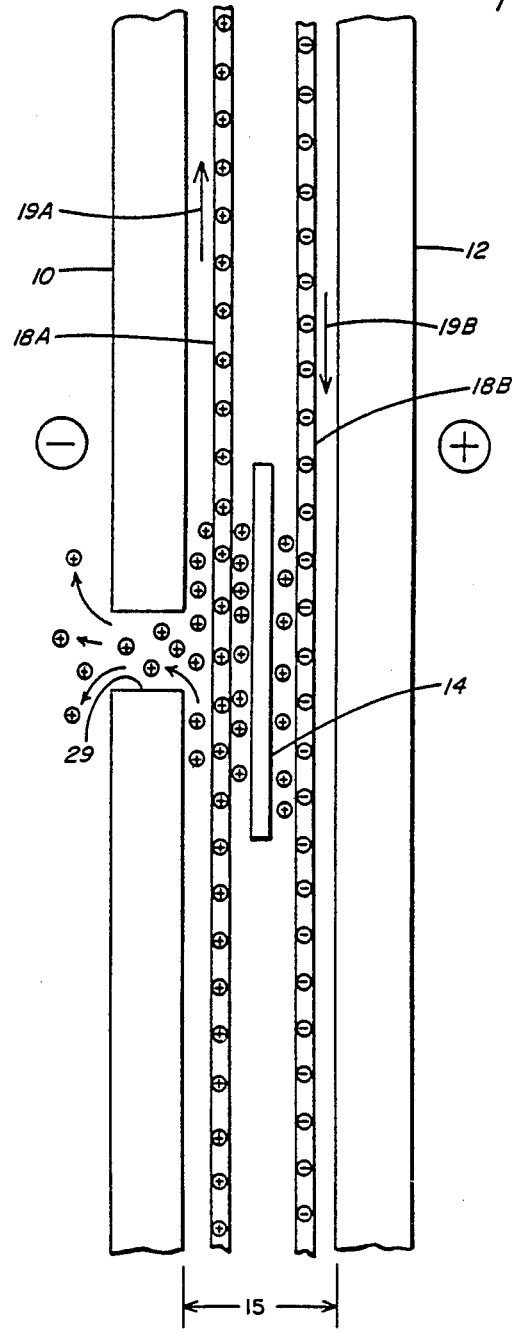

SEPARATING CONSTITUENTS OF A MIXTURE OF PARTICLES

RELATED APPLICATION

This application is a continuation-in-part of application Ser. No. 06/872,082, filed June 6, 1986 pending.

BACKGROUND OF THE INVENTION

This invention relates in general to improvements in separation processes for the physical separation of different species of the material constituents of a mixture of species, more particularly to new methods and means for increasing the respective concentrations of separated species of such constituents. The invention is applicable to a wide variety of physical mixtures, such as separating ice crystals from pulverized, frozen aqueous solution, as well as to the beneficiation of ores. It has been found to be particularly useful in the separation of impurities form coal, i.e.: coal benefication.

The present invention relates broadly to separation of dissimilar species ranging in size from macroscopic particles to molecular mixtures. Recent advances in biotechnology have allowed production of hormones, enzymes, antibodies and other biologically active materials, and large scale production of these will revolutionize the treatment of disease, the raising of plants and animals for food, and the renewable synthesis of industrial materials. Separation technology has not kept pace with the needs of the biotechnology industries. Separation and purification of these materials is the most costly and difficult aspect of making these products on a preparative scale. Scale up of laboratory techniques has allowed production, but at high cost. A low cost, effective separation technique would lower the cost of these products and enormously increase the benefits that will result.

Laboratory analytical techniques emphasize sensitivity and the detection of very low levels of material. Techniques such as chromatography, field flow fractionation (FFF) (see Giddings U.S. 3,449,938), electrophoresis, micro-sieving, molecular distillation, and liquid-liquid extraction originated in the laboratory and have limited commercial application. These separation techniques are expensive when scaled to produce commercial quantities of materials requiring high levels of separation.

Attempts have been made to scale laboratory techniques using apparatus of commercial size. Problems arise because of the difficulty of maintaining consistent flow over a large cross section. In preparative scale chromatography one way to achieve consistent flow is to use a packing with a large pressure drop, but channeling and flow maldistribution can still occur. In preparative eletrophoresis, convection currents from heating due to the applied current can disrupt the separation to such an extent that performing the separation in zero gravity in orbit is expected to be economic for some separations. The state of the art of electophoresis practice is well described in Electrophoresis '86, Proceedings of the Fifth Meeting of the International Electrophoresis Society, M. J. Dunn, ed., VCH Publishers, 1986. Chromatography can be considered to be countercurrent liquid-liquid extraction where one of the liquids is a stationary phase held on the stationary support. The stationary liquid phase never leaves the separation column and so is subject to eventual degradation, necessitating replacement. The stationary phase renders chromatography inherently a batch-type process.

Distillation uses the pressure difference between boiler and condenser to provide the driving force for moving vapor countercurrent with respect to the liquid. Many compounds with low vapor pressure are degraded at temperatures high enough to provide a vapor pressure sufficient to move the vapor at an effective mass flow rate.

The classification of particles by size is often achieved through sieving. Maintaining the dimensional accuracy of the sieve, preventing the sieve from becoming clogged, and the necessarily thin and delicate construction of fine mesh screens presents problems in operation that have limited screening practice to coarse particles.

Liquid-liquid extractin is a very powerful separation technique, but is difficult to practice when the two fluids have similar densities, high viscosities and low interfacial tension. Such fluids are commonly used to separate proteins, cell components and DNA. Aqueous polymer mixtures of different molecular weight form near-critical two phase systems that can be used to separate biological material. The state-of-the-art is well described in a book *Partitioning in Aqueous Two-Phase Systems,* edited by H. Walter et al. Academic Press, 1985. Gravity and centrifugal effects have been used to move and separate the two phases, but this is a time consuming process, and limits the number of countercurrent stages that are practical.

The constituents of coal which are considered to be "impurities" include those containing sulfur and some minerals which form non-combustible ash. Ash-forming constituents coat, foul and reduce the efficiency of heat transfer in boilers in addition to polluting the environment. Sulfur-bearing constituents contribute to environmental pollution, one form of such pollution being commonly referred to as "acid rain". As found in its natural state, coal contains varying proportions of these impurities, the proportions in any one deposit depending on the geological history of that deposit.

This invention teaches new methods and means for electrically charging and separating different species of the constituents of coal and other ores, solutions and slurries, including power-like ultra-fine particles sizes (e.g.: smaller than 100 microns), and for electrically charging a mixture which includes such ultra-fine particles, so as to enable particles of impurities and particles of coal, phosphate, solute or other desired component, or species of constituents of any such mixture, to be separated from each other in an electric field more efficiently than has heretofore been achieved on a commercial scale.

FEATURES OF THE INVENTION

It is a feature of this invention to provide a method of separating diverse mixtures so as to allow recovery of valuable component species, or to allow removal of objectionable component species.

It is still another feature of this invention to provide a method in accordance with the preceding feature which allows very difficult separations heretofore only practiced with small scale laboratory analytical methods to be practiced economically at high capacity.

It is still another feature of this invention to provide for operation independent of a gravitational field.

It is still another feature of this invention to use flow channels that are open and have low resistance to flow.

It is still another feature of this invention to provide a mechanical transport system eliminating the need for thermal convection, pneumatic or hydraulic transport, and gravity flow.

It is still another feature of this invention to provide a mechanical cleaning system to keep the interior surface of the separator clean.

It is still another feature of this invention to provide apparatus for carrying out the invention.

It is still another feature of this invention to provide a countercurrent separation method that can yield very high levels of separation.

It is still another feature of this invention to provide a separation method that is insensitive to the adverse effects of thermal convection.

It is still another feature of this invention to use a foraminous mechanical transport system to allow communication of separating species with the boundaries of the separator.

It is still another feature of this invention to provide a separation method that does not require the use of adsorbent materials.

It is still another feature of this invention to use a mechanical transport system that does not block the separation influence.

It is one feature of this invention to provide a method of separation that does not use gas to fluidize particles so as to avoid the particle size limits imposed by particle entrainment, that does not have the complexity and expense of gas handling equipment, and does not have bubbles of a fluidizing gas causing mixing within the separator.

It is another feature of the particle charging and separating embodiment of this invention to use as strong an electric field as possible, close to breakdown and without corona, and to allow the apparatus to spark over without damage and the field to quickly recover.

It is a further feature of the particle charging and separating embodiment of this invention to allow separation of mixtures of conductive particles as well as mixtures of non-conductive particles with conductive particles and mixtures of non-conductive particles.

It is still another feature of this invention to provide a separator that is substantially totally enclosed and operates substantially dust-free.

It is still another feature of this invention to avoid the use of a stationary liquid extraction phase.

It is still another feature of this invention to allow separation to be performed under conditions of laminar or turbulent flow.

It is still another feature of this invention to allow separation to be performed on chemically reacting mixtures while the reactions are proceeding.

SUMMARY OF INVENTION

According to the invention, materials are separated in a separation chamber, said separation chamber having a smaller dimension between confronting surfaces and longer dimensions in directions transverse to the smaller dimension, by admitting the mixture to be separated into the separation chamber, imposing a separation influence across the smaller dimension of the separation chamber, causing species to differentially separate across the smaller dimension of the separation chamber, mechanically moving the differentially separated layers transversely to the separation influence whereby continued application of the separation influence and continued motion of the differentially separated layers results in an integration of the separation so as to produce substantial separation across the length of the separation chamber in the direction of movement of the layers.

The present invention is continuous and can be scaled to operate at very high capacity, while maintaining very high levels of separation. In conventional, batch FFF as described by Giddings, 3,449,938, a fluid containing separable species is caused to flow through a narrow channel while a separation field is maintained across the narrow channel. The viscosity of the fluid sets up a velocity gradient in the fluid due to laminar flow, and the separation field causes the different separable species to reside at different levels and hence in different velocity streamlines, so that the fluid carries them through the channel at different rates, resulting in sequential elution of the separable species. The present invention utilizes mechanical transport of the fluid, such as with an open mesh belt, and so allows countercurrent operation of a FFF separation device. The use of an independent mechanical flow inducing device allows separation to be performed continuously, and results in a separator suitable for large scale use. The narrow channel can be made very wide to accommodate large flow rates and allow use for preparative scale separations.

Batch FFF has been studied for many years, and many types of separation fields have been utilized, and can be used in the present invention. In U.S. Pat. No. 3,449,938 Giddings claims the method of batch FFF using separation influences consisting of one of a thermal gradient, an electric field, a centrifugal force, a shear field, a gravitational field, ultrasonic vibrations, and mechanical vibrations. All of these can be used in the present invention, as well as other separation forces such as are produced by a magnetic field gradient as described by T. M. Vickrey and J. A. Garcia-Ramirez in "Magnetic Field-Flow Fractionation: Theoretical Basis", *Separation Science and Technology*, 15(6) pp 1297–1304, 1980, an electric field gradient utilizing dielectrophoresis as described by J. M. Davis and J. Calvin Giddings in "Feasibility Study of Dielectrical Field-Flow Fractionation" *Sep. Sci.*, 21(9), pp 969–989, 1986, a plasma intensity gradient, and a flow field.

The present invention is applicable to a wide range of separations problems such as the separation of emulsions such as are formed during liquid-liquid extraction, the separation of particles of different sizes, the separation of liquid-vapor mixtures such as are formed during distillation, the separation of proteins according to their charging properties due to chemical equilibrium in aqueous solutions of different pH, the separation of solid particles from a liquid such as are formed during partial crystallization, the separation of weakly magnetic particles from non-magnetic particles, the separation of cells and cell components according to their partitioning properties in two phase aqueous polymer mixtures, the separation of cells and cell components according to their dielectrophoretic properties, the separation of particles by size, the separation of magnetic fluids such as molecular oxygen or aqueous solutions of magnetic compounds. Mixtures of particle species can be separated based on the polarity of electric charge developed by particle species due to their contact charging properties. The sign of charge that a particle develops depends on its compositon and the compositon of the neighboring particles that it contacts.

BRIEF DESCRIPTION OF THE DRAWINGS

The above and other objects, features and advantages of the present invention will be better understood from a reading of the following specification in conjunction with the attached drawings in which:

FIG. 1 is a schematic illustration of a particle separating system employing a continuous belt to transport particles in two streams running in opposite directions;

FIG. 2 is an enlarged view of a portion of FIG. 1 showing a "space-charge" process of separation of particles according to their respective charges;

DETAILED DESCRIPTION OF THE DRAWINGS

Figure 3:
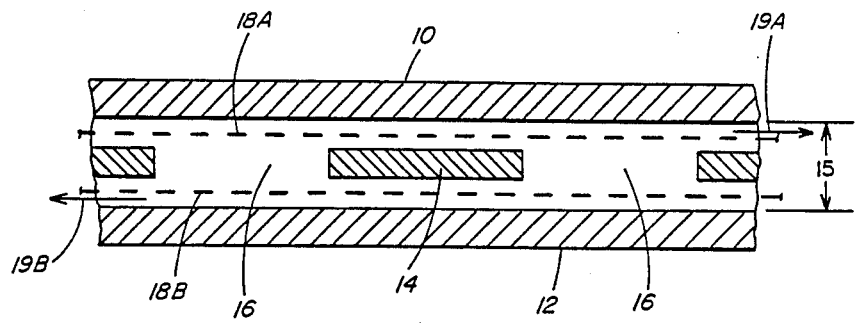
FIG. 3 is an enlarged section of a portion of FIG. 1 showing a means to provide a spatially separated sequence of alternating particle-charging zones and particle-separating electric fields.

In the embodiment of the invention useful for separating particulate materials that is illustrated in FIGS. 1-3, inclusive, an electric field is established in a thin gap 15 (about 10 mm) between two extended substantially imperforate electrodes 10 and 12, respectively. A perforated sheet 14 located between the electrodes, made of or coated with a dielectric material, has a series of holes 16 extending between the electrodes. An endless belt 18, preferably an open mesh of dielectric or dielectric-coated screen-like material (represented by dashed lines) is supported on two rollers 20, 22, respectively, one at each end of the apparatus, with respective extended sections 18A and 18B located in the spaces between the intermediate sheet 14 and the respective electrodes 10 and 12. Two tension rollers 20A and 22A, respectively, maintain the extended inter-electrode sections 18A and 18B taught. When the support rollers 20, 22 are rotated, for example, clockwise around their respective axes 21 and 23 as is indicated in FIG. 1, the inter-electrode sections 18A and 18B of the belt move in relatively opposite directions, 18A to the right and 18B to the left, as is indicated by arrows 19A and 19B, respectively, in FIG. 3.

In use, the apparatus of FIGS. 1-3, inclusive, is preferably oriented so that the extended inter-electrode sections 18A and 18B of the endless belt 18 will be in vertical planes. This can be achieved by orienting the support roller axes vertically, side-by-side, with the inter-electrode belt sections 18A and 18B extending horizontally between the rollers or, alternaively, by orienting the support roller axes horizontally, on above the other, with the inter-electrode belt sections extending vertically between them. Either of these preferred arrangement will remove the possibility that gravity will transport the particulate material under treatment between the electrodes, and through the holes 16 in the intermediate sheet 14. The particulate material to be treated (e.g: pulverized coal) is introduced into the apparatus via a slot-like opening 11 in one of the electodes 10. Separated products (e.g: coal and rejects, respectively) are taken out of the apparatus at the ends 26 and 28.

The electric field in the gap 15 will appear between the electrodes 10, 12 where the dielectric of the intermediate sheet 14 is not present, that is, where the holes 16 are located. In the regions where there is a dielectric between the electrodes, charged particles of the particulate material under treatment and ions present within the gap transport charge from an electrode to the surface of the dielectric confronting that electrode, until the potential at that surface of the dielectric is the same as the potential on the confronting electrode, whereupon electrical driving force to move charged particles in the field no longer exists. The field voltage then appears substantially entirely across the intermediate sheet 14. In this way the perforated, or "holey" intermediate sheet produces a series of alternating regions in the gap 15 which exhibit an electric field interspersed with regions which do not exhibit an electric field. Particle charging occurs in the former, and particle separating occurs in the latter.

Referring in particular to FIG. 2, a hole 29 is provided in one of the electrodes 10 through which charged particles of one species of the particles may be removed from the system. Assuming the electrodes 10, 12 are relative (−) and (+), respectively, the belt section 18A adjacent the first electrode 10 will carry positively-charged particles (product) and the belt section 18B adjacent the second electrode 12 will carry negatively-charged particles (reject). The hole 29 is adjacent an imperforate part of the intermediate sheet 14. Space charge effects due to the (+) and (−) charges on the product and reject, respectively, are substantial and have effects that can be used in this arrangement.

The (effectively) dielectric intermediate sheet 14 collects charges (negative confronting the negative electrode 10 and positive confronting the positive electrode 12) until there is no more driving force to transport charge to its surfaces; thus the E-field at the dielectric surfaces of the intermediate sheet 14 must ideally be "0". The local field between each of these surfaces and the respective confronting electrode then be determined by the space charge and increases with distance from the dielectric surface. The encircled (+) and (−) signs shown adjacent the respective dielectric surfaces of the sheet 14 represent space charges. If there is a hole in the electrode confronting one of the dielectric surfaces of the intermediate sheet 14 charged particles brought adjacent to that hole by a segment of the belt 18A or 18B moving between that surface and the hole are driven through that hole by the relevant local field. In the illustration of FIG. 2, positively-charged particles are shown leaving through the hole 29 under driving force of the local space charge field between the negatively charged electode 10 and the confronting (dielectric) surface of the intermediate sheet 14.

This local space-charge field could be increased by using for the intermediate electrode 14, or to coat one or both of its surfaces, a material which contact-charges to one sign or the other. This local space-charge field causes those particles with the highest charge to be removed, through the hole 29, for example. Particles with lesser charges, or particles charged to the opposite polarity from those which the local space-charge field will remove, are not removed, and continue on the belt 18 to be further concentrated and separated.

The local space-charge field can also be enhanced or reduced by choosing a material of construction for the belt that contact charges to the same sign or the opposite sign as the particles respectively. The sign of charge on the belt can be controlled by the material of construction of the belt and the surfaces that the belt is in contact with, including the electrodes, the intermediate sheet and the rolls.

Holes for removal of separated particles can be provided in both electrodes, adjacent imperforate portions of the intermediate holey sheet 14. However, the electodes 10, 12 are imperforate where holes 16 through the sheet 14 are between them.

The inter-electrode gap 15 being small, the inter-electrode belt sections 18A and 18B can rub on the confronting surfaces of the electrodes. This rubbing action cleans the electrodes continually, providing a self-cleaning feature of the invention.

Figure 4:
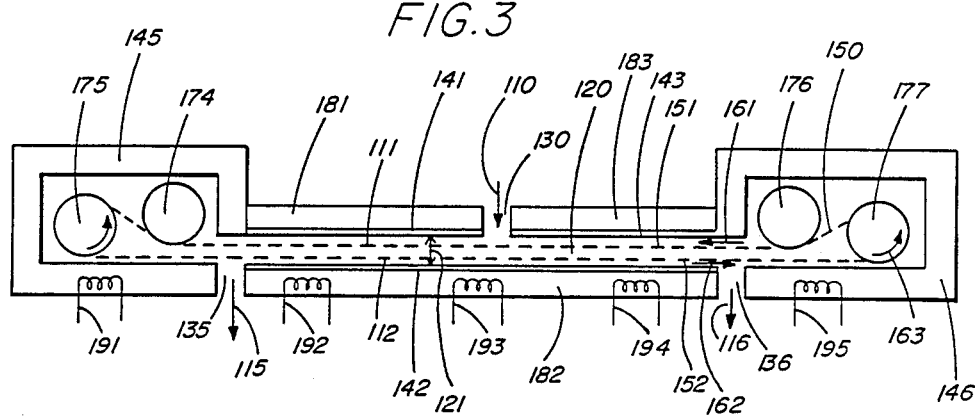
FIG. 4 is a schematic drawing of an apparatus using an electric field useful for carrying out the present invention in fluid mixtures.

With reference now to FIG. 4, a schematic diagram of an apparatus for carrying out an embodiment of the present invention, a feed mixture stream 110 is admitted to the separation chamber 120 through aperture 130 in the separation chamber boundary 141, 143. The separation chamber 120 is seen to be thin and elongated, formed by flat, parallel boundaries 141, 142, 143 which are separated by distance 121. The mixture to be separated is mechanically moved by the endless belt 150 in two streams in opposite directions 161 and 162 by sections of belt 151 and 152, respectively. The endless belt 150 is supported and driven by rollers 174, 175, 176, 177. The direction of rotation 163 being counter-clockwise as shown. An electric field is imposed across the gap 121 by potential applied between electrodes 181, 183 and 182.

As feed is introduced into separation chamber 120 and is transported in two streams by the endless belt 150 the applied electric field causes a migration of charged species across the gap 121. As the streams 111, 112 are carried in opposite directions 161 and 162 continued migration of species between streams 111 and 112 occurs resulting in a high degree of separation by the time the streams 111, 112 are carried to the exit apertures 135 and 136. The separated species are removed from the separation chamber through exit apertures in streams 115 and 116. The drive rolls are enclosed in enclosures 145 and 146 so as to prevent loss or contamination of separating materials. These enclosures support bearings and drives (not shown) used to support and rotate the rolls. Temperature controlling means 191, 192, 193, 194, 195 are used to adjust and control the temperature of the apparatus so as to maintain a desired temperature or temperature gradient across the length of separation chamber from end 145 to end 146.

FIG. 4 illustrates an embodiment of the invention useful for performing the electrophoretic separation of proteins. A solution of proteins in a suitable buffer is admitted to the apparatus through aperture 130. The charge on the individual protein molecules is controlled by the chemical reactions and the chemical equilibrium between the proteins and the fluid buffer. The positive species are acted upon by the applied electric field and migrate toward negative electrodes 181 and 183. The positive species are then transported by belt segment 151 toward the take off aperture 135. Similarly negative species migrate toward electrode 182 and are carried by belt segment 152 toward take off aperture 136. Thus a separation is made between oppositely charged species in a solution and the charge on a protein can be controlled by adjusting the pH. Heat generated by the passage of current through the solution' can be removed with temperature adjusting means 191, 192, 193, 194, 195.

It is often useful in the present invention that selective barriers 141, 142, 143, be interposed between the electrodes and the separation chamber. The purpose of these barriers is to prevent the products of electrolysis generated at the electrode surfaces from contacting the material in the separation chamber. Suitable barriers include ion exchange membranes or porous filtration membranes such as are described by L. F. Kesner et al, "Performance Characteristics of Electrical Field-Flow Fraction in a Flexible Membrane Channel" *Anal Chem*, 48, 13, Nov. 1976, pp 1834. Isolation of the products of electrolysis is often best achieved by circulating a fluid (not shown) around the electrodes that is kept from mixing with material in the separation chamber.

It is also often useful in the present invention to interpose a selective barrier between belt segment 151, 152. The purpose of this barrier is to reduce the effects of mixing influences while not adversely affecting the separation. For the present embodiment shown in FIG. 4, interposing a porous membrane between the belt segments will reduce the convective mixing of the separating fluids, but will not impede the movement of charged species by the electric field. Suitable barriers can be made from any porous material that is compatible with the fluids being separated.

Referring now to FIG. 3, during the separation, influences can develop that counteract the separation influence and limit the separation that can be achieved. When separating charged species, the spatial separation of positively and negatively charged species produces an electric field that counters the applied separation field. This adverse effect can be reduced by interposing a barrier 14 between belt segments 18a, 18b which blocks the motion of all species and allows the excess positive or negative charge to be neutralized by charges from a confronting surface, which then allows for renewed separation to continue in region 16 after the barrier 14.

In the present invention the barriers are useful in many embodiments. When separating dissimilar particles using an alternating periodic magnetic field dissimilar particles will contact charge according to their surface properties and the spatial separation of the dissimilar particles due to the magnetic field will also result in a spatial charge separation and will produce an electric field that will impede the separation. Interposing barriers will allow these electrical charges to dissipate without deterioration of performance.

Figure 5:
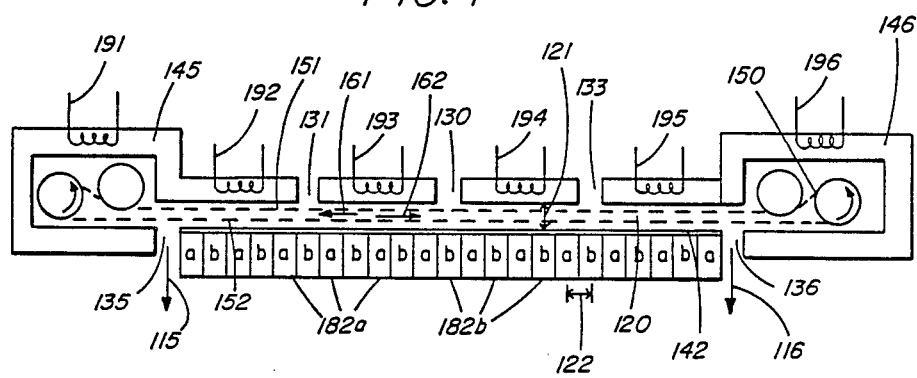
FIG. 5 is a schematic drawing of an alternate embodiment of the present invention using either electric or magnetic fields.

With reference now to FIG. 5, an alternate embodiment of the present invention is shown in a schematic diagram. The operation of this embodiment differs from that shown in FIG. 4 by the type of separating influence that is used to effect the separation. The separation influence is produced by an alternating periodic potential produced by the array of field generating elements 182a and 182b. These elements are separated by gap 122 and generate a separation field that decreases in strength with distance from the surface of the array. The field generating array is separated from the separation chamber 120 by the chamber wall 142. The array produces a net attractive force that decreases with distance and hence is stronger in the vicinity of belt segment 152 and weaker in the vicinity of belt segment 151. Species with higher susceptibility to the separation influence are attracted toward the array and displace species with lower susceptibility which are moved away from the array. Thus the more susceptible species are moved into the vicinity of belt segment 152 where they are moved by belt segment 152 toward exit port 136 and form product stream 116.

Similarly low susceptibility species migrate toward the vicinity of belt segment 151 where they are moved by belt segment 151 toward exit port 135 and form product stream 115.

The embodiment of the present invention that uses an alternating periodic electric potential on field generating elements 182a and 182b uses the principles of dielectrophoresis. The state of the art is well described by H. A. Pohl in *Perry's Chemical Engineer's Handbook Sixth Edition*, D. W. Green ed, McGraw Hill, 1984 and in Pohl's book *Dielectrophoresis* Cambridge, 1978. These two references describe the theory and the many applications that a dielecrophoretic separation can be used for. The present invention has greater utility than those previously described because it is a countercurrent process. Dielectrophoresis can be used to separate droplets of one fluid from another, particles from a fluid, bubbles of gas from a fluid or particles of differing dielectric constant.

Temperature control means are used to control the temperature, either uniformly, or as a function of distance between exit ports 115 and 116.

One application of this embodiment is to separate weakly magnetic particles from non-magnetic particles. A mixture of particles is introduced into feed port 130 and a magnetic potential is applied between field generating elements 182a and 182b, for example by making the faces of elements 182a that confront chamber wall 142 north magnetic poles, and the confronting faces of elements 182b south magnetic poles. The intensity of the magnetic forces can be controlled with the intensity of the individual field generating elements, the spacing between elements 122, the thickness of chamber wall 142 and chamber dimension 121.

When utilizing a magnetic field gradient for separation it is often useful to incorporate a magnetic material into transport belt 150 so that under the influence of the magnetic field from field generating elements 182a, 182b, the magnetic material will focus the field and generate high field gradients that move along with the transport belt and facilitate the transport of magnetic particles. It is also convenient to periodically and sequentially reduce each element's magnetic fields to zero so as to allow highly magnetic particles to be flushed out.

Another application of the embodiment illustrated in FIG. 5 is to separate two phases, such as dispersed droplets of water in an oil phase. The emulsion is introduced into feed port 130 and an electric potential is applied between field generating elements 182a and 182b, for example by making the faces of elements 182a that confront chamber wall 142 positive, and the confronting faces of elements 182b negative. The intensity of the electric forces can be controlled with the intensity of the individual field generating elements, the spacing between elements 122, the thickness of chamber wall 142 and chamber dimension 121.

Other applications are to separate solid particles from a liquid, bubbles of gas from a liquid, dissimilar solid particles, solid particles from a gas or liquid droplets from a gas. It should be noted that while separating a gas from a liquid, temperature controlling means 191, 192, 193, 194, 195, 196 can be used to affect the vapor liquid equilibrium and for example convert liquid being transported by belt segment 152 into vapor which is then transported in the opposite direction by belt segment 151. Simultaneously the vapor being transported by belt segment 151 can be condensed into liquid which is then transported by belt segment 152. Thus, the present invention can be used to separate species of different relative volatility by supplying heat through temperature controlling means 196 so as to vaporize liquid in enclosure 146 and remove heat through temperature controlling means 191 so as to condense vapor in enclosure 145. The countercurrent transport of vapor and liquid is similar to distillation practice, but the present embodiment operates independent of gravity and does not use centrifugal effects or a pressure drop to transport liquid or vapor. Similarly the present embodiment can be used to separate crystals of a material from a freezing mixture and to practice countercurrent fractional crystallization.

Another application of the present embodiment is to separate species in a fluid by a process known as countercurrent extraction. In this application a fluid mixture is introduced through aperture 131 and an extracting fluid is introduced through aperture 133. The extracting fluid is moved in direction 161 by belt segment 151. The fluid mixture is carried in direction 162 by belt segment 152. The two fluids are in intimate contact and by appropriate choice of extracting fluid, the desired species can be recovered. The species need not be dissolved in one of the fluids. For example, a slurry or pulverized coal in oil is fed into aperture 133 and water is introduced into aperture 131. The hydrophyllic-ash-bearing minerals are extracted into the water phase and removed through aperture 136 while the hydrophobic coal remains in the oil phase and is recovered at aperture 135.

The present embodiment is especially suitable for performing countercurrent separations of biological materials. Biologically active materials can be separated from fermentation broth, or disrupted cells. Protein, RNA or DNA can be extracted by using different fluid phases that have different affinities for the various desired materials. Separations can be done with whole cells, either by using fluids with different affinities for different cells or cell components, or alternatively by applying an AC potential to field generating means 182a, 182b, of the proper frequency so as to deflect the desired cells preferentially. If the AC potential is increased sufficiently to get electrical breakdown in the separation chamber 120, the gradient of intensity of the partially ionized plasma created by the dielectric discharge can be used to separate particles with different surface electrical properties.

Figure 6:
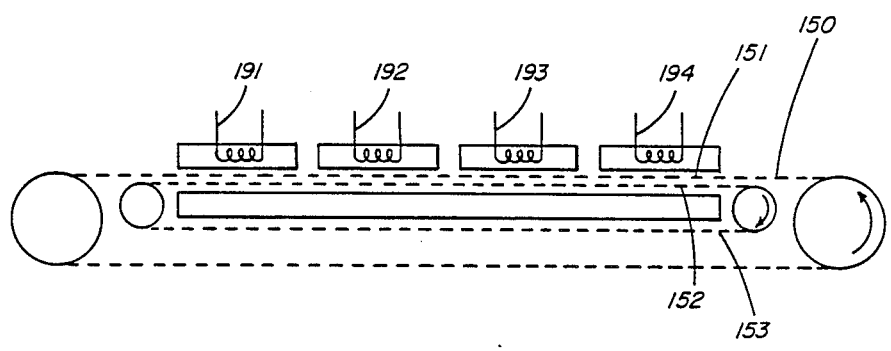
FIG. 6 is a schematic drawing of an alternate embodiment of the present invention using a shear field.

With reference now to FIG. 6 of the drawings showing an embodiment utilizing two belts. The two transport belts 150, 153 are moved at different speeds, so that belt segments 151, 152 move at different speeds. The different belt speeds create an asymmetic shear field. The shear field can be used as a separation influence to move particles to where they can be transported by belt segment 151 or 152 in the appropriate direction. A sheared dispersion of particles exerts a force normal to the plane of shear. This pressure is (according to Bagnold, Phil. Trans. R. Soc,. Ser. A, 249, 235–297 (1956)) equal to $$P = 0.041\sigma(\lambda D)^2 \left(\frac{du}{dy}\right)^2$$

$$\lambda = \text{the linear concentration} = \frac{1}{\left(\frac{0.64}{C}\right)^{\frac{1}{3}} - 1}$$

$D$ = particle diameter
$u$ = particle velocity parallel to directions 161 or 162
$y$ = length coordinate parallel to length 121
$\sigma$ = particle density
$C$ = volumetric concentration The foraminous belt segments 151, 152 are open and do not block the movement of particles. Particles migrate due to the particle pressure developed by the shear field.

The use of a shear gradient is well known in the mineral dressing industry where flowing film concentrators or sluices have been used for centuries, and are well described by F. B. Michell in *SME Mineral Processing Handbook*, N. L. Weiss ed., published by Aime, 1985. Conventional practice is to use a water slurry flowing down an inclined surface. The present invention utilizes a mechanical transport system and so requires no water or other fluid that can cause the loss of very fine particles.

The present invention is countercurrent, so that both recovery and purity can be made very high in a single device.

Thus belt segments 151, 152 moving at different speeds produce an asymmetrical shear field that causes particles to migrate based on their size, density and concentration. The classification of particles can be practiced in a fluid, such as water or air, and can also be practiced in a vacuum. The effects of shear induced classification of particles based on their size can be observed on particles ranging from fine clay particles transported by water to sand and gravel carried by flowing rivers, to large boulders carried by glaciers. Similarly, the present invention can utilize shear to classify particles of any size by using appropriately sized apparatus. Droplets of liquid in a fluid can behave as particles and are influenced by a shear field. The present embodiment can be used to separate droplets from an emulsion and to practice countercurrent extraction and distillation. Bubbles of gas behave as particles and so can be separated from a fluid. Bubbles of gas can attach to particles, as in froth flotation, and a bubble with attached particles can be influenced by the shear field and carry attached particles with it.

The high degree of shear and mechanical agitation produced by the belt results in very good heat transfer between the temperature controlling means 191, 192, 193, 194 and particulate material in the separator. The heating and cooling of fine particulate material can be accomplished during the separation, for example, for the separation of water from a particulate material, heat can be applied to vaporize the water and the particles can be separated from the gaseous water. Similarly heat can be moved between particles of different particle size if small cold particles and large hot particles are introduced at different apertures and are moved by the belts in a countercurrent manner. The small cold particles extract heat from the large hot particles.

The two belts 150, 153 can be of different constructions in terms of compositon, thickness or weave, and the belt composition can be chosen to promote the selective mechanical transport of the components to be separated by choosing a material for the belt that has an affinity for one of the components under the conditions of separation. For example, if belt 153 is constructed of a magnetizable material and belt 150 is constructed of a nonmagnetic material and if a magnetic field is applied to the separation chamber, then the magnetic strands will product magnetic field gradients that will attract the magnetic particles will be transported by the nonmagnetic belt in the other direction. Other belt materials can be chosen with different selective affinities to promote other separations, for example by incorporating an ion-exchange resin into the belt material, ions can be selectively transported. Similarly, other adsorbent such as molecular sieves, stationary liquid phases such as are used in chromatography, bound monoclonal antibodies, materials to produce high electric field gradients, materials that contact charge to one sign or another, materials of different wetability so that droplets can be held by surface tension can all be used to promote the selective transport of certain components.

It is often desirable to clean the belts after they have passed outside the separation chamber. Components can be cleaned off the belts by using for example a jet of air, also known as an air knife, centrifugal force as the belt moves over a roll, a fluid spray, a fibrous brush, vibration, gravitational attraction, a fluid to dissolve or chemically extract adhering components such as acid in the case of cationic ion-exchange resins in the belt or buffers of the correct ionic strength to remove bound proteins, hot air to remove bound water or other volatile species.

Figure 7:
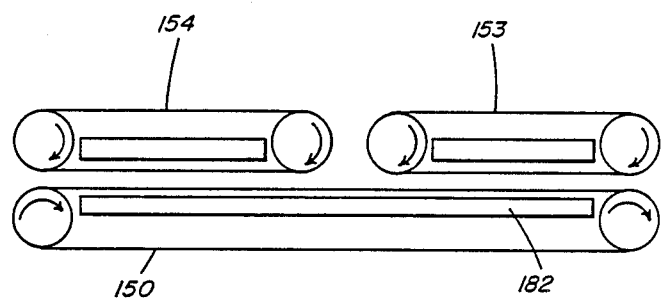
FIG. 7 is a schematic drawing of an alternate embodiment of the present invention using imperforated transport belts.

With reference now to FIG. 7 of the drawings showing an embodiment with imperforate transport belts 150, 153, 154. The transport belts form the separation chamber boundaries. The belts should be made of a material that does not interfere with the separation influence produced by field generating assembly 182. For example, if an alternating periodic electric potential is used as the separation influence, then the belts should be made of a non-conductive material so as to avoid shielding the separation chamber from the field generating means.

Figure 8:
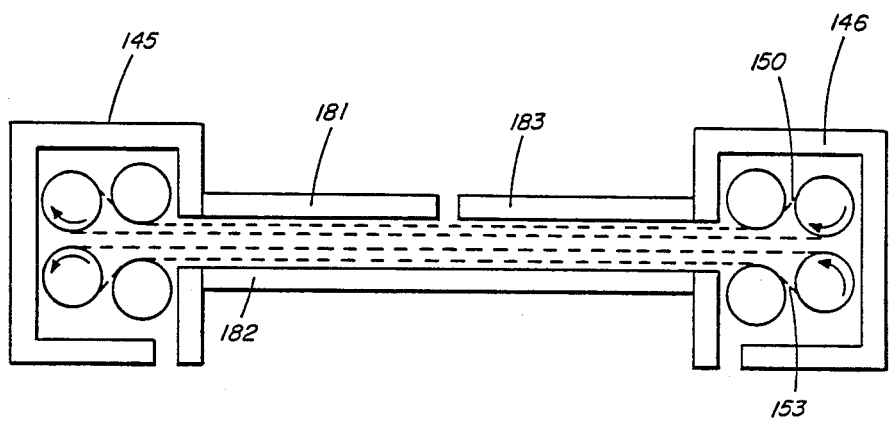
FIG. 8 is a schematic drawing of an alternate embodiment of the present invention useful for isoelectric eletrophoresis.

Referring now to FIG. 8 which shows an embodiment useful for separating a narrow fraction. The two mechanical transport belts 150, 153 generate a countercurrent circulation with one stream near the center of the separation chamber and two counter-flowing streams near the separation chamber boundaries. An AC alternating periodic electric potential produced by field generating means 182, can be used to attract some species, and a different frequency AC alternating periodic potential produced by field generating means 181, 183 can be used to attract other species. Species that are not attracted by the two different frequencies used remain in the center of the separation chamber and are transported by the belts toward enclosure 145 and species that are attracted by either field are moved toward the walls of the separation chamber and transported by the belts to enclosure 146.

Other separation fields can be used also, for example if field generating means 181, 182, 183, generate a uniform DC electric field across the separation chamber, and if a solution of proteins is buffered so that the pH of the solution corresponds to the isoelectric point of a protein in the mixture, and the mixture is introduced into the separation chamber, then the electric field deflects charged species toward either electrode and away from the center. The protein that is at its isoelectric point is uncharged and has no net motion in the electric field, and so is transported by the belt segments in the center of the separation chamber toward separator end 145.

Figure 9:
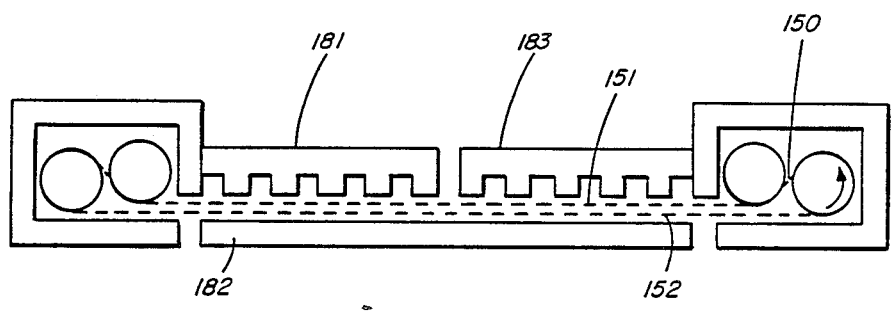
FIG. 9 is a schematic drawing of an alternate embodiment of the present invention using asymmetric confronting surfaces to produce a shear field.

Referring now to FIG. 9 which illustrates an embodiment of the invention using textured surfaces as shear field generating means. Field generating means 181, 183 has protruding elements that confine the belt 150 in the separation chamber. The average distance form the belt to surfaces 181, 183 is seen to be greater than the average distance from the belt to surface 182. Shear is a velocity gradient. Belt segments 151 and 152 are moving at the same velocity, but in opposite directions. The distance from moving belt to stationary surface and the velocity difference determines the shear. Thus, because the distance from belt segment 151 to surface 181, 183 is greater than the distance from belt segment 152 to surface 182, the shear is correspondingly less between belt segment 151 and surfaces 181, 183. This difference in shear can be used to separate particles and droplets as discussed earlier.

Figure 10:
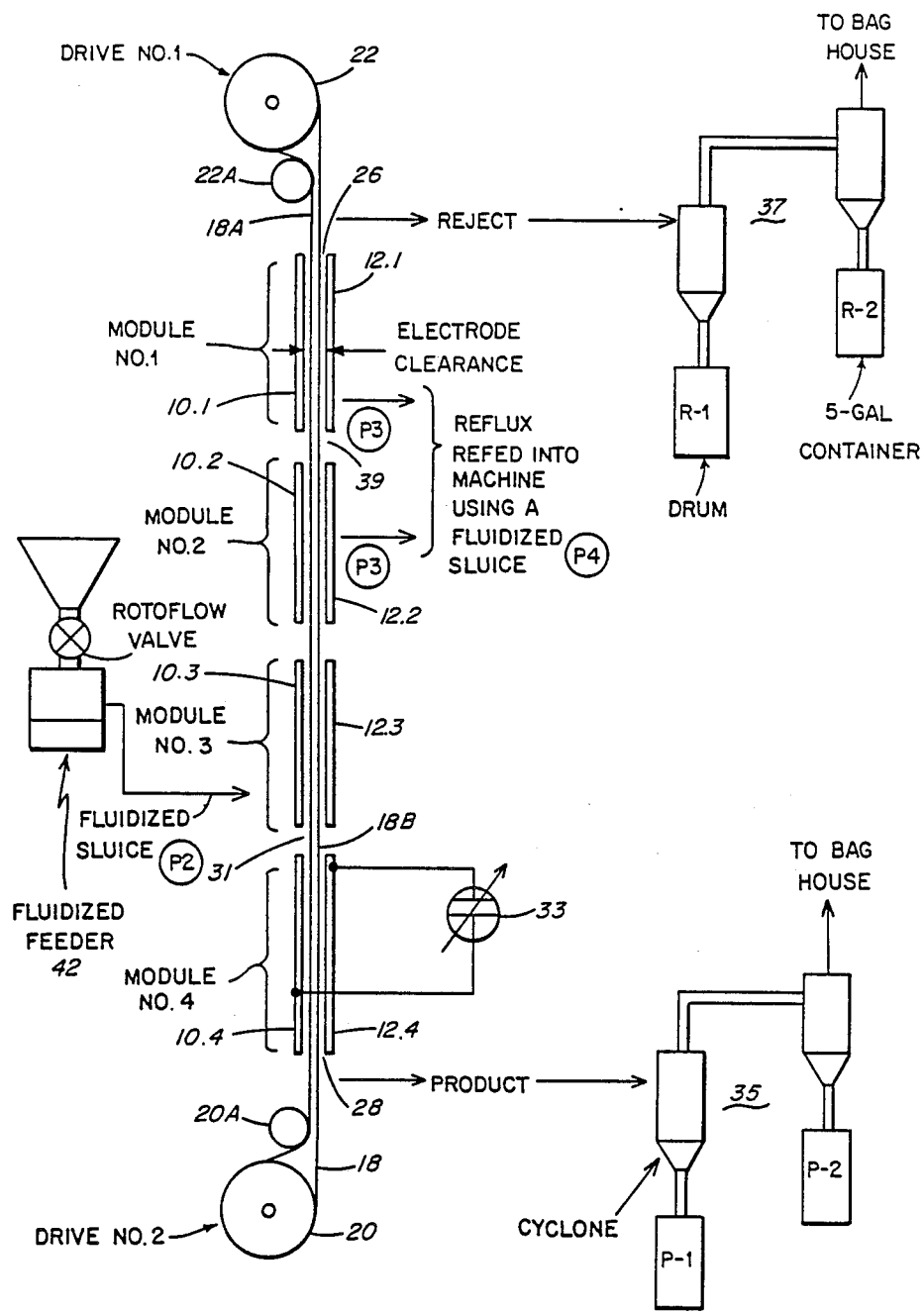
FIG. 10 is a schematic illustration of another continuous belt system.

The embodiment of the invention illustrated in FIG. 10 presents the particle charging and separating apparatus of FIG. 1 in a preferred vertical orientation. Also shown are auxiliary components of a complete coal-treating system. The holey sheet 14 is not included in this embodiment of the apparatus, which relies on substantially continuous contact-charging and electrostatic particle separation, in place of the alternate charging and separating steps that are carried out in the embodiment of the apparatus that is illustrated in FIGS. 1–3. Parts of the apparatus that are common to FIGS. 1 and 10 bear the same reference characters.

The electrostatic field is established between several respective sequentially-arrayed modules of plates 10.1, 12.1; 10.2, 12.2; 10.3, 12.3; and 10.4, 12.4 being labelled modules #1, #2, #3 and #4, respectively, on the drawing. The field modules are spaced apart along the apparatus, and a supply of particles to be separated can be introduced in any space between adjacent electrodes, such as in the space 31 between electrodes 10.3 and 10.4. Each module has its own power supply, of which only one 33 is schematically represented connected to the electrodes 10.4 and 12.4 of module #4. Product is taken from the lower end 28 to cyclone separator station 35 producing product batches P-1 and P-2. Reject is taken from the upper end 26 to a cyclone separator station 37 producing reject batches R-1 and R-2. Product can be removed from the belt by centrifugal force as the belt goes over roll 20. If desired, reflux of reject may be refed into the apparatus in a space such as the space 39 between electrodes 12.1 and 12.2 between modules #1 and #2. In this embodiment, the oppositely moving belt surfaces 18A and 18B are in close proximity to each other, and they produce a large velocity gradient between the oppositely-polarized field electrodes, which in turn produces a high degree of shear in the ambient gas, which promotes vigorous particle-to-particle contact and enhances particle charging between the electrodes.

The belt 18 is the only moving part in the belt separator apparatus of FIGS. 1 and 10. This belt has several functions common to both embodiments of the apparatus. The first is that of moving particles along the surface of each electrode 10, 12. The second function is that of keeping the electrodes clean by sweeping and scouring the surfaces. In both embodiments the belt allows particles to transfer from one stream to another under the influence of the electric field, and so minimally interferes with particle trajectories, which are through the holes 16 when the intervening holey sheet 14 is present.

According to the invention, the belt 18 has substantial open areas, which may be realized with an openly woven fabric, a foraminous material, an open knit material, or the like. The belt material should not adversely affect the electric field between the electrodes, so a material that is substatially non-conductive, so a not so short out the electrodes, should be chosen. For best performance the belt should be as thin as possible to minimize electrode spacing. To have long life the belt material should be abrasion resistant and have a high strength, should have a low coefficient of friction, be resistant to conditions of temperature and humidity that are present in the machine, and should have a structure which easily allows for fabricarion of seamless belts.

Figure 12:
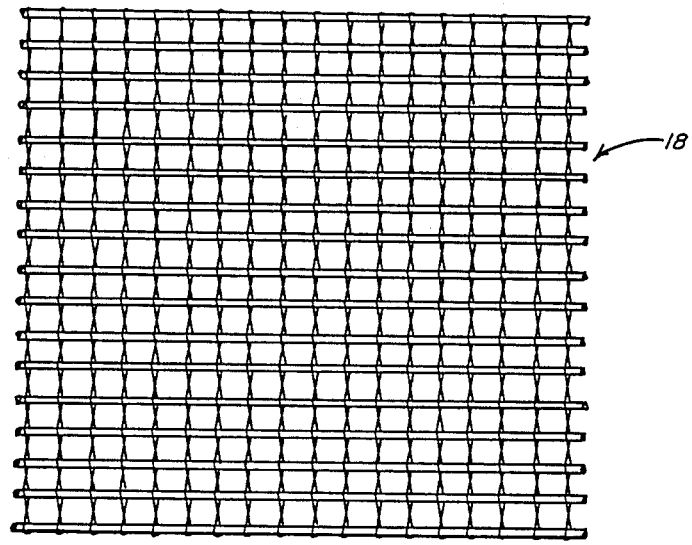
FIG. 12 shows a portion of a mesh belt in full size.

Examples of materials that have been tested and found useful for the purposes of the invention include a 4×4 leno weave made from strands of Kevlar (Trademark) coated with Teflon (Trademark), a swatch of which is shown in FIG. 12, in actual size. This material will withstand high temperatures, is physically strong and is resistant to chemical deterioration. Another material (not illustrated) is a monofilament polyethylene approximately 7×11 leno weave. This latter material, although not as strong as the "Kevlar/Teflon" material illustrated, is more abrasion resistant, easier to fabricate into belts and is cheaper. An ideal material should have properties found in an ultra-high molecurar weight polyethylene fiber which has very high strength, very good abrasion resistance and a low coefficient of friction. The hole sizes and materials mentioned here are illustrative only. It is contemplated that other materials and hole sizes will be useful, and some may yield better separation results than have been achieved up to now. Thus, smaller holes may provide better separation is some instances. The dielectric properties of the belt material will bear a relation to the field strength that can be used, and should be chosen, within the other constraints, to allow high field strengths between the elecrodes.

Scaling up belt separator apparatus as shown in FIGS. 1 and 10 can be done by increasing the width of the belt 18. For maximum effectiveness, the belt should be loaded with feed material uniformly over its entire width. A convenient way to do this has been with a fluid bed distributor, schematically shown at 42 in FIG. 10. The function of this distributor is to fluidize pulverized material so that it behaves like a liquid and flows to form a horizontal surface and uniformly overflows a level dam (not shown) to produce a uniform flow of material over the width of the belt. This fluid bed also aerates the feed and breaks up clumps of material so that operation of the separator apparatus is more consistent and uniform. Another function of the separator apparatus is to trap high density tramp material such as pieces of metal that may inadvertently become mixed with the feed.

Figure 11:
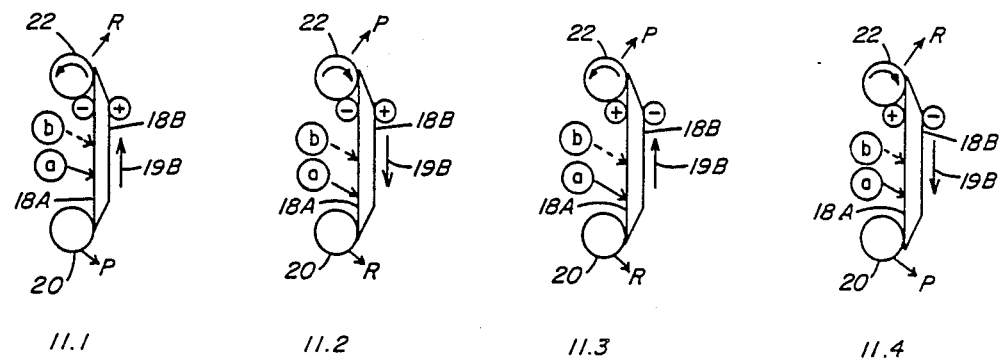
FIG. 11 illustrates a variety of configurations in which belt systems can be operated.

Belt-separator apparatus according to the invention can be used also in any of four electrical and mechanical configurations, which are shown in FIG. 11, at 11.1 to 11.4, respectively. The variation are belt direction and electrode polarity. The capital letters "P" and "R" represent product and reject, respectively. The electrode polarities are indicated by symbols (+) and (−), each encircled. An arrow 19B indicates the direction of belt motion. Two feed locations, (a) and (b), each encircled, are shown in each configuration. In an embodiment according to FIG. 10 which is 16 feet high, consisting of four 30" long electrode modules, in which the straight sections 18A and 18B of the belt between the electrodes are each 10' long, feed location (a) is approximately 32" above the lower edge of the bottom module #4, and feed location (b) is about 62" above the same reference. In a test of this embodiment, using a pulverized coal feed, processed in each of the illustrated four configurations, the following preliminary conclusions were drawn:

1. Best results are obtained when the feed coal does not traverse through the belt (i.e.: the negative electrode is on the feed side);
2. Best results are obtained when the reject is transported to the top of the apparatus;
3. Feed locations (a) or (b) did not significantly impact the performance of the apparatus.

Configuration 11.1 yielded the best sulfur and ash reductions with nearly the highest fraction of the feed reporting to the product.

These conclusions and results do not necessarily apply to other coals, or to other materials, or to recycling the product or to other materials, or to recycling the product or the reject. Similarly, other embodiments using different separation influences can be operated in a varity of configurations.

Figure 13:
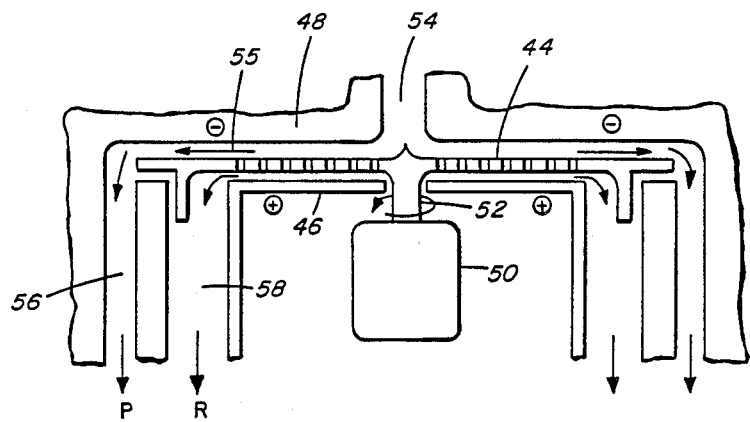
FIG. 13 is an axial section through an illustration of another embodiment of the invention employing a rotating disc.

The apparatus of FIG. 10 performs a continuous countercurrent separation process which separated particles one from another depending on their surface charges. FIG. 13 illustrates another embodiment of the invention which performs a co-current separation process using a rotating holey disk 44 and centrifugal effects to mechanically transport the feed material. The disk 44 is located between two electrodes 46, 48 which in use are oppositely polarized, and a motor 50 is used to rotate the disk on a spindle 52. As in FIG. 1, the holey disk 44 is made either of a dielectric material, or has a dielectric coating on its surfaces. The feed material (e.g.: powdered coal) is fed to the apparatus through a hole 54 in one of the electrodes and substantially coaxial with the spindle 52, so that the rotating disk transports the feed material radially outward between the electrodes. The resulting process is similar to that performed by the apparatus of FIG. 1, but in this case the holey dielectric sheet moves between stationary electrodes, and no other component is needed to transport the feed material between the electrodes. Also, the two streams of charged particles on either side of the holey disk move in the same direction—i.e.: the process is "co-current", indicated by an arrow 55.

In use, feed material is introduced at the center 54 and is picked up by a central impeller (disk 44) where it is thrown out radially. As the feed material moves outward it is accelerated and subjected to a high shear gradient (the disk may have a speed of 100 ft/sec at the circumference and the electrodes are stationary). This shear gradient produces large amounts of turbulence and particle-particle contact that causes contact, e.g.: "triboelectric" charging, at the particle surfaces. The moving holey disk 44 alternately allows the electric field from the electrodes to cause separation and then blocks the field to allow charging. Product (P) and reject (R), for example, will exit via concentric passage 56, 58, respectively.

The holey disk separator according to FIG. 13 was found to have the characteristic that the stream that passes through the disk is more concentrated than the stream that does not. For example in FIG. 13 the separator is configured so that if coal is fed to the top of the disk the minority material (ash) is collected on the bottom. If the polarity is reversed then the product is much cleaner and is collected on the bottom, but the rejects are much less concentrated. For a complete countercurrent cascade this characteristic can be used advantageously to reduce the number of stages needed for concentrating the rejects in a feed coal in order to get very high Btu recoveries. The exact number of stages will be determined experimentally for the particular coal under consideration.

The various products and rejects from the various machines are reprocessed to obtain additional separation of ash minerals from coal. Streams are either fed to a new machine, or combined with a feed stream that is similar in composition. In this way separation is not lost by mixing streams of differing composition. It should be noted that the material (either product or reject) that passes through the "holey" disk is sufficiently enriched that it is advantageous to skip an intermediate machine when transporting material toward the product or reject side of the cascade. With this arrangement individual separators that are co-current can be arranged in a countercurrent cascade.

Figure 14:
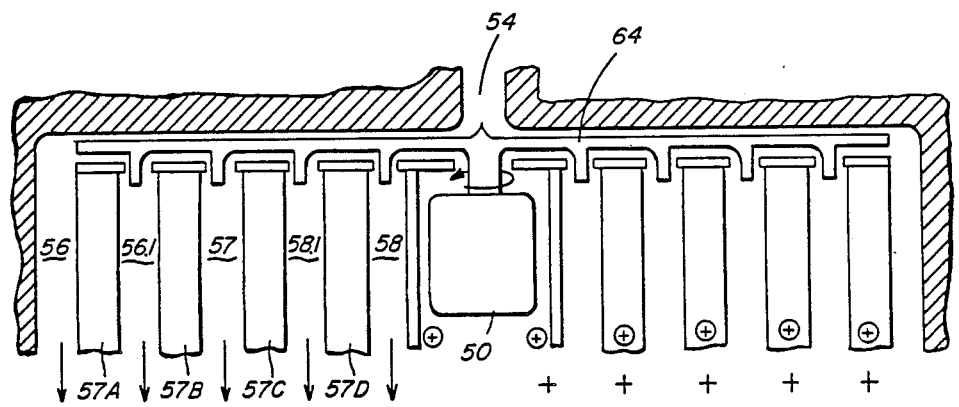
FIG. 14 is an axial section through an illustration of a multi-stage separator developed from the embodiment of FIG. 13.

FIG. 14 shows a multi-stage version of the holey disk separator developed from the embodiment of FIG. 13. A holey disk 64 cooperates with a concentric group of annular electrodes 57A, 57B, 57C, 57D to feed an inner collection passage 58, and outer collection passage 56, and intermediate collection passages 56.1, 57 and 58.1. In this configuration the outermost collection passage 56 collects product, and the progressively-inner collection passages 56.1; 57 and 58.1 collect reject with the concentration of ash being progressively higher toward the center passage 58. Two such machines can be connected together to give a very clean product and a very concentrated reject. A further refinement (not illustrated) would be to recycle material to various feed locations located at different distances from the center, so that streams of different composition are not mixed during operation.

Figure 15:
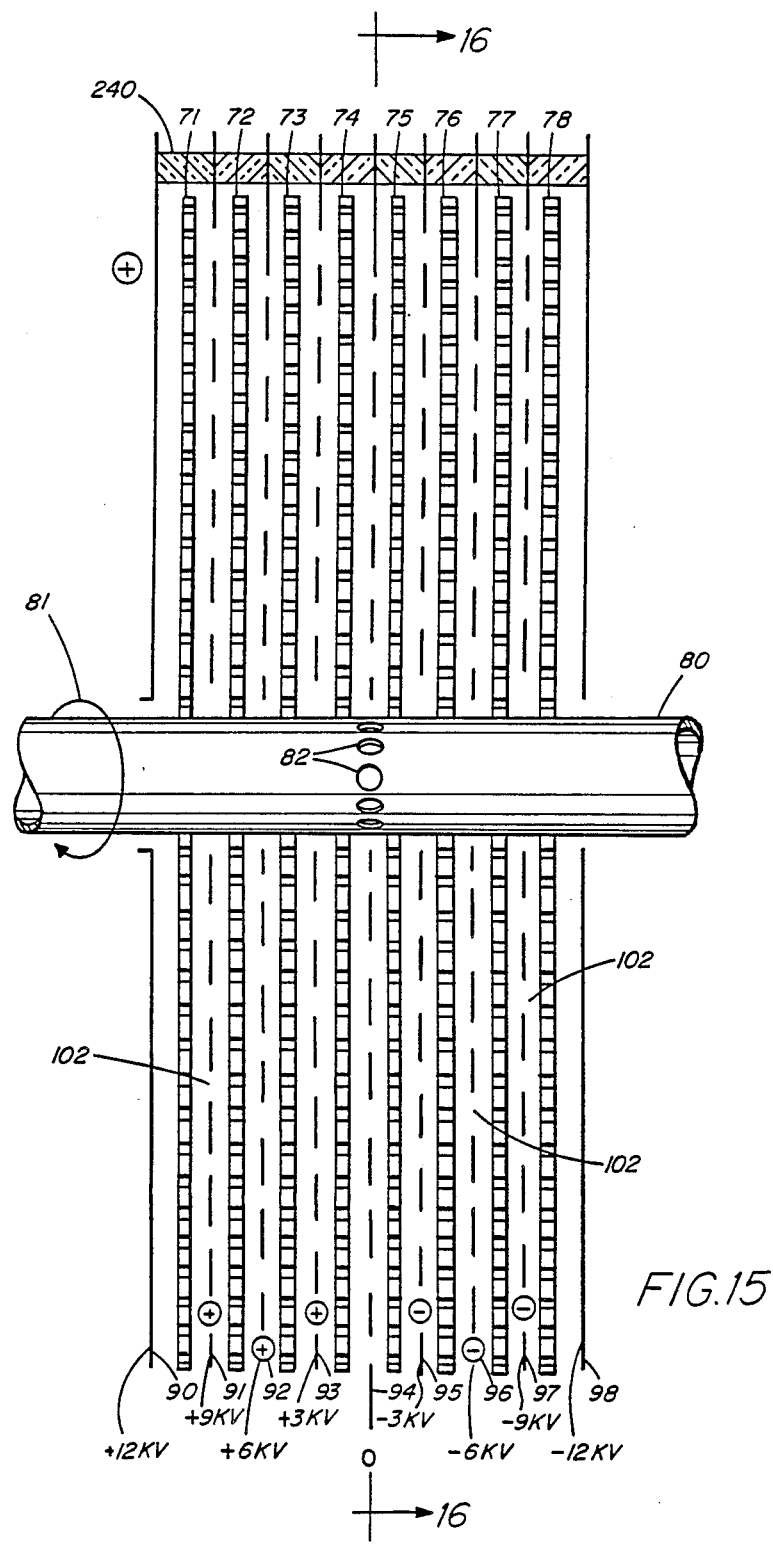
FIG. 15 illustrates another embodiment of the invention.
Figure 16:
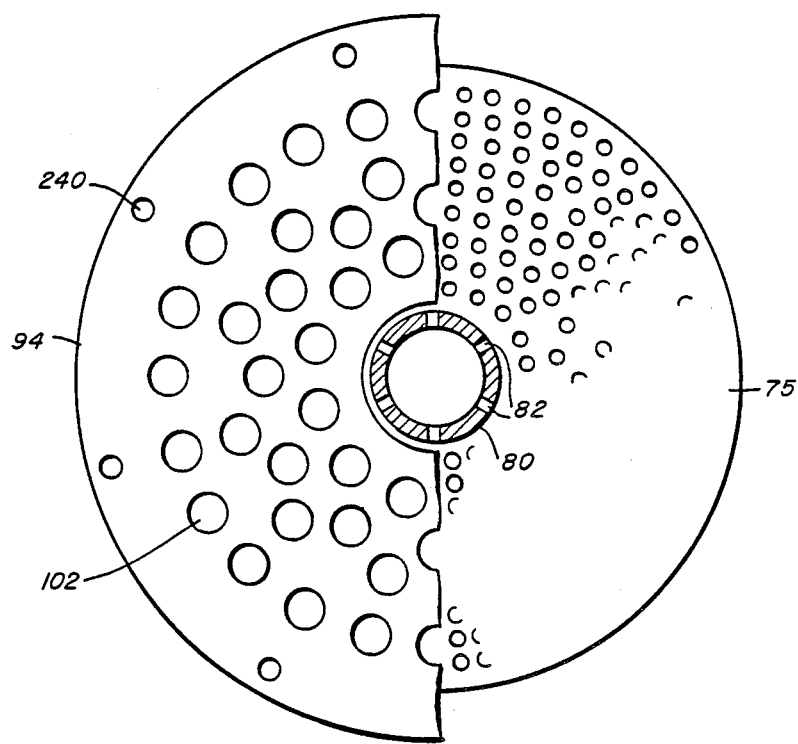
FIG. 16 is a section on line 10—10 of FIG. 15.

FIG. 15 show schematically a multi-stage separator employing a stack of holey dielectric disks 71–78, inclusive, arrayed parallel to each other spaced apart along a central feed tube 80, A circumferential array of feed holes 82 is provided in the tube wall, spaced between the two intermediate adjacent disks 74 and 75. An electrode 91 is located between the first two adjacent disks 71, 72. A second eletrode 92 is located between the second two adjacent disks 72, 73, and so forth for electrodes 93–97. End electrodes 90 and 98 are near the outer surfaces of the first holey disk 71 and the last holey disk 78, respectively. The electrodes are spaced from the feed tube 80, being supported separately from it on dielectric spacers 240, as is indicated also in FIG. 16.

To provide a series of E-fields across each holey disk, the electrodes may be given progressive potentials, for example, as is indicated in the drawing. Thus, the middle electrode 94 may have "O" potential, electrodes 95–98 to one side of it may have progressively more negative potentials, and electrodes 93–90 to its other side may have progressively more positive potentials. Some of the electrodes between holey disks are fitted with apertures 102 allowing the material being processed to pass back and forth between the positive side and the negative side of the electrode.

In use, the feed tube 80 is rotated, as is indicated by an arrow 81 and particulate feed (e.g.: coal) is fed into it, at one end. Feed coal exits the feed tube via feed holes 82 and is cast radially outward by the disks 71–78 rotating on the feed tube. The electrode 90–98 are stationary, and are polarized as shown in the figure with the voltage on each electrode being different. The endmost electrode at the reject take off end 90 has the highest voltage. The voltage on successive electrodes is lower, so that there is substantially constant electric field, both in sign and magnitude, between each pair of adjacent electrodes. This electric field causes charged particles of product and reject to migrate in opposite axial directions.

Having now described a limited number of embodiments of the present invention, it should now be apparent to those skilled in the are that numerous other embodiments and modifications thereof are contemplated as falling within the scope of the present invention as defined by the appended claims.

What is claimed is:

1. A method of separating different components of a mixture of a material in a separation chamber without requiring pneumatic, hydraulic or gravitational conveyance comprising the steps of:
   a. admitting said material into the separation chamber, said separation chamber having means defining confronting surfaces spaced more closely than the respective lengths of said confronting surfaces;
   b. impressing a separation influence toward at least one of said confronting surfaces of said separation chamber wherein said separation influence is chosen from the list of electric field, electric field gradient, magnetic field, magnetic field gradient, shear field, acceleration field, temperature gradient, vibration, gravitation field, flow field, shear gradient, concentration gradient, chemical affinity;
   c. separating said different components in the direction of said separation influence according to their relative influencability to said separation influence;
   d. mechanically moving components of like net influencability in streams each of unlike net influencability near each other transversely to said separation influence, said streams being in communication parallel to said separation influence, so as to transfer a portion of at least one of said components to another of said respective streams of virtue of the continued action of said separation influence as said streams progress transversely to said separation influence;
   e. removing separated streams from said separation chamber.

2. The method of claim 1 whereby the electric field is generated in a fluid electrolyte and is isolated from the separation chamber by a barrier that is permeable to charge carriers but substantially impermeable to the products of electrolysis.

3. A method as set forth in claim 1 wherein said streams are mechanically moved in opposite directions.

4. A method as set forth in claim 1 wherein the step of separating includes providing more than one separation influence generating means to generate said separation influence.

5. A method as set forth in claim 1 wherein said separation influence is impressed in a spatially periodic manner.

6. A method as set forth in claim 1 wherein the step of admitting includes providing more than one feed material admission opening in the separation chamber.

7. A method as set forth in claim 6 wherein feed materials of different composition are each admitted to different regions of the separation chamber at different distances along the direction of motion of said streams.

8. A method as set forth in claim 1 wherein the step of mechanically moving components includes generating regions of shear within the separation chamber.

9. A method as set forth in claim 1 wherein said streams are mechanically moved in opposite directions at different speeds.

10. A method as set forth in claim 1 wherein the step of mechanically moving components includes generating regions with different levels of shear within said separation chamber.

11. A method as set forth in claim 1 wherein the step of impressing a separation influence includes providing multiple electrodes to generate said separation influence.

12. A method as set forth in claim 1 further including the step of providing a barrier interposed between said separating streams.

13. A method as set forth in claim 1 wherein one of said components is a liquid.

14. Apparatus for separating different components of a mixture of material comprising:
   a separation chamber having means defining confronting surfaces spaced more closely than the respective lengths of said confronting surfaces;
   means to apply a separation influence across the smaller dimension of the separation chamber toward one of said confronting surfaces where said separation influence is chosen from the list of electric field, electric field gradient, magnetic field, magnetic field gradient, shear field, acceleration field, temperature gradient, vibration, gravitation field, flow field, shear gradient, concentration gradient, chemical affinity;
   means to mechanically transport material without requiring pneumatic, gravitational or hydraulic conveyance in streams running transversely to said separation influence, and with said separation influence deflecting influence components from said streams in accordance with their influencability; and means to remove separated components from said separation chamber.

15. Apparatus as set forth in claim 14 wherein said mechanical transport means comprises an endless belt of foraminous construction.

16. Apparatus as set forth in claim 14 whereby the electric field is generated in a fluid and is isolated from the separation chamber by a barrier that is permeable to charge carriers but substantially impermeable to the products of electrolysis.

17. Apparatus as set forth in claim 14 wherein said mechanical transport means and said confronting surfaces are provided by imperforate endless transport belts.

18. Apparatus as set forth in claim 14 wherein a barrier is interposed between said streams.

19. Apparatus as set forth in claim 18 wherein said barrier is permeable to at least one of said different components.

20. Apparatus as set forth in claim 14 wherein one of said components is a liquid.

21. Apparatus for separating different components of a mixture of material comprising:
    a separation chamber having means defining confronting surfaces spaced more closely than the respective lengths of said confronting surfaces;
    means to apply a separation influence across the smaller dimension of the separation chamber toward one of said confronting surfaces;
    means to mechanically transport material in streams running transversely to said separation influence, and with said separation influence deflecting influence components from said streams in accordance with their influencability; and
    means to remove separated components from said separation chamber;
    wherein more than one separation influence developing means is provided.

22. Apparatus for separating different components of a mixture of material comprising:
    a separation chamber having means defining confronting surfaces spaced more closely than the respective lengths of said confronting surfaces;
    means to apply a separation influence across the smaller dimension of the separation chamber toward one of said confronting surfaces;
    means to mechanically transport material in streams running transversely to said separation influence, and with said separation influence deflecting influence components from said streams in accordance with their influencability; and
    means to remove separated components from said separation chamber;
    wherein more than one means to introduce a material mixture into said separation chamber is provided.

23. A method of separating different components of a mixture of a material in a separation chamber comprising the steps of:
    a. admitting said material into the separation chamber, said separation chamber having means defining confronting surfaces spaced more closely than the respective lengths of said confronting surfaces;
    b. impressing a separation influence toward at least one of said confronting surfaces of said separation chamber;
    c. separating said different components in the direction of said separation influence according to their relative influencability to said separation influence;
    d. mechanically moving components of like net influencability in streams each of unlike net influencability near each other transversely to said separation influence, said streams being in communication parallel to said separation influence, so as to transfer a portion of at least one of said components to another of said respective streams of virtue of the continued action of said separation influence as said streams progress transversely to said separation influence;
    e. removing separated streams from said separation chamber;
        where the temperature of regions in the separation chamber is regulated as a function of distance in the direction of motion of said streams.

24. The method of claim 23 where temperature differences between said regions of said separation chamber are sufficient to produce a phase change affecting at least one of said components as said streams transport said components between said regions.

25. The method of claim 24 where the phase change is chosen from the list of: vaporization, condensation, solidification, melting, sublimation, adsorption, desorption, dissolution, precipitation.

26. A method of separating different components of a mixture of a material in a separation chamber comprising the steps of:
    a. admitting said material into the separation chamber, said separation chamber having means defining confronting surfaces spaced more closely than the respective lengths of said confronting surfaces;
    b. impressing a separation influence toward at least one of said confronting surfaces of said separation chamber;
    c. separating said different components in the direction of said separation influence according to their relative influencability to said separation influence;
    d. mechanically moving components of like net influencability in streams each of unlike net influencability near each other tansversely to said separation influence, said streams being in communication parallel to said separation influence, so as to transfer a portion of at least one of said components to another of said respective streams of virtue of the continued action of said separation influence as said streams progress transversely to said separation influence;
    e. removing separated streams from said separation chamber;
        where two different materials are each admitted to different regions of the separation chamber at different distances along the direction of motion of said streams, so as to develop a countercurrent flow of components from the two admitted materials between said admitting regions so as to facilitate the transfer of a least one component from one of said streams to another of said streams.

27. Method of claim 26 where the pairs of different materials are chosen from the list of: liquid and gas, two substantially immiscible liquids, two materials of near critical composition, two polymer solutions of different molecular weights, a fluid and a particulate material, two particulate materials, a slurry and a fluid, an emulsion and a fluid, a catalyst and a reacting fluid, a slurry and a gas, two particulate materials at different temperatures.

28. Apparatus for separating different components of a mixture of material comprising:
- a separation chamber having means defining confronting surfaces spaced more closely than the respective lengths of said confronting surfaces;
- means to apply a separation influence across the smaller dimension of the separation chamber toward one of said confronting surfaces;
- means to mechanically transport material in streams running transversely to said separation influence, and with said separation influence deflecting influence components from said streams in accordance with their influencability; and
- means to remove separated components from said separation chamber;
- wherein said separation chamber incorporates temperature controlling means.

29. Apparatus for separating different components of a mixture of material comprising:
- a separation chamber having means defining confronting surfaces spaced more closely than the respective lengths of said confronting surfaces;
- means to apply a separation influence across the smaller dimension of the separation chamber toward one of said confronting surfaces;
- means to mechanically transport material in streams running transversely to said separation influence, and with said separation influence deflecting influence components from said streams in accordance with their influencability; and
- means to remove separated components from said separation chamber;
- where said separation influence is developed by an alternating periodic electric potential.

30. Apparatus for separating different components of a mixture of material comprising:
- a separation chamber having means defining confronting surfaces spaced more closely than the respective lengths of said confronting surfaces;
- means to apply a separation influence across the smaller dimension of the separation chamber toward one of said confronting surfaces;
- means to mechanically transport material in streams running transversely to said separation influence, and with said separation influence deflecting influence components from said streams in accordance with their influencability; and
- means to remove separated components from said separation chamber;
- where said separation influence is developed by an alternating periodic magnetic potential.

31. Apparatus for separating different components of a mixture of material comprising:
- a separation chamber having means defining confronting surfaces spaced more closely than the respective lengths of said confronting surfaces;
- means to apply a separation influence across the smaller dimension of the separation chamber toward one of said confronting surfaces;
- means to mechanically transport material in streams running transversely to said separation influence, and with said separation influence deflecting influence components from said streams in accordance with their influencability; and
- means to remove separated components from said separation chamber;
- where said separation influence is a shear gradient developed by the interaction of said mechanical transport means and said confronting separation chamber walls.

32. A method of separating different components of a mixture of a material in separation chamber comprising the steps of:
- a. admitting said material into the separation chamber, said separation chamber having means defining confronting surfaces spaced more closely than the respective lengths of said confronting surfaces;
- b. impressing a separation influence toward at least one of said confronting surfaces of said separation chamber;
- c. separating said different components in the direction of said separation influence according to their relative influencability to said separation influence;
- d. mechanically moving components of like net influencability in streams each of unlike net influencability near each other transversely to said separation influence, said streams being in communication parallel to said separation influence, so as to transfer a portion of at least one of said components to another of said respective streams of virtue of the continued action of said separation influence as said streams progress transversely to said separation influence;
- e. removing separated streams from said separation chamber;
  - where a component - component interaction chosen from the list of adsorption, ion exchange, antibody binding, pH equilibrium, solvent extraction, phase equilibrium, vapor liquid equilibrium, phase partitioning capillary adhesion, bubble attachment, wetability is used to enhance the recovery of a desired component.

33. A method of separating different components of a mixture of a material in a separation chamber comprising the steps of:
- a. admitting said material into the separation chamber, said separation chamber having means defining confronting surfaces spaced more closely than the respective lengths of said confronting surfaces;
- b. impressing a separation influence toward at least one of said confronting surfaces of said separation chamber;
- c. separating said different components in the direction of said separation influence according to their relative influencability to said separation influence;
- d. mechanically moving components of like net influencability in streams each of unlike net influencability near each other transversely to said separation influence, said streams being in communication parallel to said separation influence, so as to transfer a portion of at least one of said components to another of said respective streams of virtue of the continued action of said separation influence as said streams progress transversely to said separation influence;
- e. removing separated streams from said separation chamber;
  - wherein said streams are mechanically moved by an endless transport belt.

34. A method as set forth in claim 33 wherein at least one of said components is held to said belt.

35. A method as set forth in claim 34, wherein said at least one of said components held to said belt is held as a result of a mechanism chosen from the list of adsorption, magnetic attraction, electrostatic attraction, antibody binding, ion exchange, surface tension.

36. A method as set forth in claim 33 wherein said different components are removed from said transport belt outside the separation chamber.

37. A method as set forth in claim 33 wherein said different components are removed from said belt using a method from the list of centrifugal force, air knife, fiber brush, gravitational attraction, electrostatic forces, fluid spray, dissolving fluid.

38. Apparatus for separating different components of a mixture of material comprising:
- a separation chamber having means defining confronting surfaces spaced more closely than the respective lengths of said confronting surfaces;
- means to apply a separation influence across the smaller dimension of the separation chamber toward one of said confronting surfaces;
- means to mechanically transport material in streams running transversely to said separation influence, and with said separation influence deflecting influence components from said streams in accordance with their influencability; and
- means to remove separated components from said separation chamber;
- wherein said mechanical means furthermore removes adhering layers of particles from said confronting surfaces.

39. A method of separating different components of a mixture of a material in a separation chamber comprising the steps of:
- a. admitting said material into the separation chamber, said separation chamber having means defining confronting surfaces spaced more closely than the respective lengths of said confronting surfaces;
- b. impressing a separation influence toward at least one of said confronting surfaces of said separation chamber;
- c. separating said different components in the direction of said separation influence according to their relative influencability to said separation influence;
- d. mechanically moving components of like net influencability in streams each of unlike net influencability near each other transversely to said separation influence, said streams being in communication parallel to said separation influence, so as to transfer a portion of at least one of said components to another of said respective streams of virtue of the continued action of said separation influence as said streams progress transversely to said separation influence;
- e. removing separated streams from said separation chamber;
- providing a barrier interposed between said separating streams;
- wherein said barrier is permeable to at least one of said components.

40. Apparatus for separating different components of a mixture of material comprising:
- a separation chamber having means defining confronting surfaces spaced more closely than the respective lengths of said confronting surfaces;
- means to apply a separation influence across the smaller dimension of the separation chamber toward one of said confronting surfaces;
- means to mechanically transport material in streams running transversely to said separation influence, and with said separation influence deflecting influence components from said streams in accordance with their influencability; and
- means to remove separated components from said separation chamber;
- wherein more than one means to remove separated components from said separation chamber is provided.

41. A method of separating different components of a mixture of a material in a separation chamber comprising the steps of:
- a. admitting said material into the separation chamber, said separation chamber having means defining confronting surfaces spaced more closely than the respective lengths of said confronting surfaces;
- b. impressing a separation influence toward at least one of said confronting surfaces of said separation chamber;
- c. separating said different components in the direction of said separation influence according to their relative influencability to said separation influence;
- d. mechanically moving components of like net influencability in streams each of unlike net influencability near each other transversely to said separation influence, said streams being in communication parallel to said separation influence, so as to transfer a portion of at least one of said components to another of said respective streams of virtue of the continued action of said separation influence as said streams progress transversely to said separation influence;
- e. removing separated streams from said separation chamber,
- wherein one of said components of the mixture is a liquid.

42. Apparatus for separating at least two different components of a mixture comprising:
- a separation chamber having means defining confronting surfaces spaced more closely than the respective lengths of said confronting surfaces;
- means to apply a separation influence across the smaller dimension of the separation chamber toward one of said confronting surfaces;
- means to mechanically transport material in streams running transversely to said separation influence, and with said separation influence deflecting influence components from said streams in accordance with their influencability; and
- means to remove separated components from said separation chamber,
- wherein one of said components is a liquid.

* * * * *